US012797351B2

(12) United States Patent
Expósito Tarrés et al.

(10) Patent No.: US 12,797,351 B2
(45) Date of Patent: Nov. 17, 2026

(54) ABSCISIC ACID FOR THE TREATMENT OF SKIN DISEASES

(71) Applicant: VYTRUS BIOTECH, S.L., Terrassa (ES)

(72) Inventors: Òscar Expósito Tarrés, Terrassa (ES); Albert Jané Font, Terrassa (ES); Sara Laplana Lasierra, Terrassa (ES); Maria Mas Duarte, Terrassa (ES); Tarik Ruiz Medina, Terrassa (ES); Ana Gallego Palacios, Terrassa (ES); Daniel Luna Bistuer, Terrassa (ES); Isabel Magdalena Ramos Rodríguez, Sant Feliu de Llobregat (ES)

(73) Assignee: VYTRUS BIOTECH, S.L., Terrassa (ES)

( * ) Notice: Subject to any disclaimer, the term of this patent is extended or adjusted under 35 U.S.C. 154(b) by 1102 days.

(21) Appl. No.: 17/046,764

(22) PCT Filed: Apr. 11, 2019

(86) PCT No.: PCT/EP2019/059350
§ 371 (c)(1),
(2) Date: Oct. 9, 2020

(87) PCT Pub. No.: WO2019/197580
PCT Pub. Date: Oct. 17, 2019

(65) Prior Publication Data

US 2021/0161842 A1 Jun. 3, 2021

(30) Foreign Application Priority Data

Apr. 12, 2018 (EP) .................................... 18382250

(51) Int. Cl.

| | |
|---|---|
| ***A61K 31/277*** | (2006.01) |
| ***A61K 31/19*** | (2006.01) |
| ***A61K 31/192*** | (2006.01) |
| ***A61K 31/215*** | (2006.01) |
| ***A61K 36/746*** | (2006.01) |
| ***A61P 17/06*** | (2006.01) |
| ***A61P 17/10*** | (2006.01) |

(52) U.S. Cl.
CPC ............ *A61K 31/19* (2013.01); *A61K 31/192* (2013.01); *A61K 31/215* (2013.01); *A61K 36/746* (2013.01); *A61P 17/06* (2018.01); *A61P 17/10* (2018.01); *A61K 2236/11* (2013.01)

(58) Field of Classification Search
None
See application file for complete search history.

(56) References Cited

U.S. PATENT DOCUMENTS

| | | | | |
|---|---|---|---|---|
| 2003/0100480 A1* | 5/2003 | Smith | ....................... | C12P 7/64 514/1 |
| 2017/0151152 A1 | 6/2017 | Beri | | |

FOREIGN PATENT DOCUMENTS

| | | | | |
|---|---|---|---|---|
| JP | 2002212052 A * | 7/2002 | | |
| JP | 2004035454 A * | 2/2004 | | |
| JP | 2008074725 A * | 4/2008 | | |
| KR | 2003-0057205 A | 7/2003 | | |
| WO | WO-2006023654 A2 * | 3/2006 | ............. | A61K 31/19 |
| WO | WO2013040556 | 3/2013 | | |
| WO | WO 2015/161860 A1 | 10/2015 | | |

OTHER PUBLICATIONS

Matsuda et al. (Study of the Anti-Photoaging Effect of Noni (*Morinda citrifolia*). Melanoma—From Early Detection to Treatment. Published Jan. 30, 2013) (Year: 2013).*
Plyuta et al. "Effect of salicylic, indole-3-acetic, gibberellic, and abscisic acids on biofilm formation by *Agrobacterium tumefaciens* C58 and *Pseudomonas aeruginosa* PAO1" Applied Biochemistry and Microbiology, vol. 49, pp. 706-710 (2013).
Qidwai et al. "Comprehensive evaluation of pharmacological properties of *Olea europaea* L. for Cosmeceuticals prospects" Clinical Phytoscience vol. 3, Article No. 12 (2017), pp. 1-7.
Soni et al. "Antibacterial Activity of *Morinda citrifolia* Linn Fruits for Acne Inducing Pathogens" International J. of Pharmacy & Pharmaceutical Research 2016, vol. 8, issue 1, pp. 208-214.
Vaughn et al. "Effects of Turmeric (*Curcuma longa*) on Skin Health: A Systematic Review of the Clinical Evidence" Phytotherapy Research, 2016, vol. 30, Issue 8, pp. 1243-1264.
International Search Report and Written Opinion mailed on May 17, 2019 for Application No. PCT/EP2019/059350, 15 pages.
Nakamizo, et al: "Commensal bacteria and cutaneous immunity", Semin Immunpathol, Oct. 18, 2014; 8 pages; DOI10.1007/s00281-014-0452-6.
Powers, et al: "Microbiome and pediatric atopic dermatitis", The Journal of Dermatology 2015; vol. No. 42, pp. 1137-1142.
Valins, et al: "The expression of Toll-like Receptors in Dermatological Diseases and the Therapeutic effect of current and newer Toll-like Receptors modulators", Journal of Clinical Aesthetic Dermatology, Sep. 2010; vol. 3, No. 9, pp. 1-10.
Wang, et al: "Skin Microbiome: An Actor in the Pathogenesis of Psoriasis", Chinese Medical Journal, Jan. 5, 2018; vol. 131, No. 1, pp. 95-98.
West, el at: "Efficacy of a Morinda citrifolia Based Skin Care Regimen", Current Research Journal of Biological Sciences, Apr. 5, 2012; vol. 4, No. 3, pp. 310-314.

* cited by examiner

*Primary Examiner* — Layla Soroush
(74) *Attorney, Agent, or Firm* — Squire Patton Boggs (US) LLP

(57) ABSTRACT

The invention relates to a new use of abscisic acid, either a pharmaceutically acceptable salt or ester of abscisic acid, for the treatment and/or prevention of a skin disease cursing with microbial biofilm formation and/or with dysbiosis of skin microbiota. In particular, it is for use in the treatment of psoriasis, acne and atopic dermatitis. The invention also discloses new pharmaceutical compositions comprising abscisic acid.

12 Claims, No Drawings

ABSCISIC ACID FOR THE TREATMENT OF SKIN DISEASES

CROSS REFERENCE TO RELATED APPLICATIONS

This application is a 35 U.S.C. § 371 application of International Application No. PCT/EP2019/059350, filed on Apr. 11, 2019, which claims the benefit of European Patent Application EP 18382250.1 filed on Apr. 12, 2018, the entireties of which are hereby incorporated by reference.

Present invention relates to the field of treatment of skin disorders with different symptoms, and in which microbiota on skin has a particular role.

BACKGROUND ART

There are many skin disorders with different and multiple symptomologies. Examples of these include acne, in all of its forms, psoriasis and atopic dermatitis. Skin is in mammals and in particular in human, the body's largest organ and is home to diverse and complex variety of innate and adaptive immune functions that protect against pathogenic invasion. Tissue-specific responses have been explored in-depth in barrier tissues, such as skin and the gastrointestinal tract that are constitutively colonized by highly diverse and site specific microbiota. Skin commensal bacteria (such as *Staphylococcus epidermidis*) modulate skin immune cell function and induce protective immunity to pathogens. However, it is widely known that dysbiosis (imbalance of microbial flora) may contribute to the induction of many of the skin pathologies (see Nakamizo et al., "Comensal bacteria and cutaneous immunity", Semin Immunpathol-2014, DOI10.1007/s00281-014-0452-6).

For example, in the case of acne, a multifactorial skin disorder, hormonal imbalances, stress, pollution and other events can cause an imbalance of the different key microbial players. In particular, there is an increase of the population of *Propionibacterium acnes* (*P. acnes*) and of *Staphylococcus aureus* (*S. aureus*) in detrimental of *Staphylococcus epidermidis* (*S. epidermidis*). Acne is a global disorder, manly associated to puberty but nowadays increasing also on adults. Acne, also known as acne vulgaris, is a long-term skin disease that occurs when hair follicles are clogged with dead skin cells and oil from the skin. Thus, in acne vulgaris, the primary process is sebaceous hyperplasia and lipid release into the follicular lumen, which leads to comedo formation and overgrowth of *P. acnes* and *S. aureus*. It is characterized by blackheads or whiteheads, pimples, papules, pustules, cists, nodules, oily skin, and possible scarring. It primarily affects areas of the skin with a relatively high number of oil glands, including the face, upper part of the chest, and back. The resulting appearance can lead to anxiety, reduced self-esteem and, in extreme cases depression. Genetics is thought to be the primary cause of acne in 80% of cases. The role of diet and cigarette smoking is controversial. During puberty, in both sexes, acne is often brought on by an increase in hormones such as testosterone. Many treatment options for acne are available, including lifestyle changes, medications, and medical procedures. Eating fewer simple carbohydrates such as sugar may help. Treatments applied directly to the affected skin, such as azelaic acid, benzoyl peroxide, and salicylic acid, are commonly used. Antibiotics and retinoids are available in formulations that are applied to the skin and taken by mouth for the treatment of acne. However, resistance to antibiotics may develop as a result of antibiotic therapy and antibiotics may also lead to imbalance of commensal microbiota.

Psoriasis is a long-lasting autoimmune disease characterized by patches of abnormal skin. These skin patches are typically red, itchy, and scaly. Psoriasis varies in severity from small, localized patches to complete body coverage. There are five main types of psoriasis: plaque, guttate, inverse, pustular, and erythrodermic. Plaque psoriasis, also known as psoriasis vulgaris, makes up about 90 percent of cases. It typically presents as red patches with white scales on top. Psoriasis is also a multifactorial disorder and many are the pathologic mechanisms leading to the several forms of expression of it. It is generally thought to be a genetic disease that is triggered by environmental factors: The cause of psoriasis is not fully understood, but a number of theories exist. Beside genetic exposition there is also acknowledged the role of lifestyle (chronic infections, stress, and changes in season and climate). Others that might worsen the condition include hot water, scratching psoriasis skin lesions, skin dryness, excessive alcohol consumption, cigarette smoking, and obesity). Also microbes are thought to play a crucial role. Psoriasis may be worsened by skin or gut colonization with *Staphylococcus aureus, Malassezia, Streptococcus* and *Candida albicans*. Although further studies are required to establish an association between the cutaneous microbiome and psoriasis, current research suggests that the microbiome in patients with psoriasis is distinct from that of healthy controls (see Wen-Ming et al, "Skin Microbiome: An Actor in the Pathogenesis of Psoriasis", Chin Med J (Engl). 2018, vol. no. 131(1), pp.: 95-98). Psoriasis is characterized by an abnormally excessive and rapid growth of the epidermal layer of the skin. Skin cells are replaced every 3-5 days in psoriasis rather than the usual 28-30 days. These changes are believed to stem from the premature maturation of keratinocytes induced by an inflammatory cascade in the dermis involving dendritic cells, macrophages, and T cells (three subtypes of white blood cells). These immune cells move from the dermis to the epidermis and secrete inflammatory chemical signals (cytokines) such as interleukin-36γ, tumor necrosis factor-α, interleukin-1β, interleukin-6, and interleukin-22. These secreted inflammatory signals are believed to stimulate keratinocytes to proliferate. One hypothesis is that psoriasis involves a defect in regulatory T cells, and in the regulatory cytokine interleukin-10. Due to the complexity of the disorder, psoriasis is mainly being faced using highly hydrating compositions. While no cure is available for psoriasis, many treatment options exist. Topical agents (corticosteroid preparations, and emollients such as such as mineral oil, petroleum jelly, calcipotriol) are typically used for mild disease, phototherapy for moderate disease, and systemic agents (methotrexate, cyclosporine, hydroxycarbamide, fumarates such as dimethyl fumarate, and retinoids) for severe disease.

Another example of skin disorder in which dysbiosis of skin microbiota is demonstrated is in atopic dermatitis. Atopic dermatitis (AD), also known as atopic eczema, is a type of inflammation of the skin (dermatitis). It results in itchy, red, swollen, and cracked skin (xerosis). Clear fluid may come from the affected areas, which often thicken over time. Scratching worsens symptoms and affected people have an increased risk of skin infections. Many people with atopic dermatitis develop hay fever or asthma. The cause of AD is not known, although there is some evidence of genetic, environmental, and immunologic factors. The skin microbiome has also been implicated in the pathogenesis of AD. Again, a localized pathogen and a constituent of general skin microbiota, *Staphylococcus aureus* (*S. aureus*) were shown to be involved in the local skin inflammation (see: Nakamizo et al., supra; Powers et al, "Microbiome and pediatric atopic dermatitis", Journal of Dermatology 2015, vol. no. 42, pp.: 1137-1142). Treatment involves avoiding things that make the condition worse, daily bathing with application of a moisturizing cream afterwards, applying steroid creams when flares occur, and medications to help with itchiness. Things that commonly make it worse include wool clothing, soaps, perfumes, chlorine, dust, and cigarette smoke. Phototherapy may be useful in some people. Steroid pills or creams based on calcineurin inhibitors may occasionally be used if other measures are not effective. Antibiotics (either by mouth or topically) may be needed if a bacterial infection develops. Dietary changes are only needed if food allergies are suspected.

Other skin disorders, such as seborrheic dermatitis, dandruff, folliculitis, contact dermatitis and rosacea are also disorders of high complexity where the skin microbiota plays a relevant role in its pathogenesis. As above exposed, although many are the products for the treatment of all these complex skin disorders, there is still a need of additional compositions and products to face them.

SUMMARY OF INVENTION

Inventors have surprisingly realized that abscisic acid (abbreviated ABA) and compositions comprising it, was able to inhibit quorum sensing in several bacterial species (gram positive and gram negative bacteria, as well as in fungus genera). Quorum sensing (QS) is the name given to the communication mode between individuals of some bacterial and fungus cells, intra- and interspecies. By means of quorum sensing, the microorganisms can "sense" how many cells are in the surroundings to form colonies and finally films, the so-called biofilms, mainly intraspecies. But quorum sensing is also used between different species to finally evolve to a mutual collaboration or to competition. Quorum sensing communication is performed through volatile biochemicals called quormones or autoinducers (AIs), synthesized and secreted by bacteria that diffuse away into the surroundings. The neighboring bacteria (or microorganisms) detect these AIs by means of QS receptors. The most complex and clinically relevant behavior regulated by QS is virulence. Thus, when environment changes in a surface where the bacteria or fungus are (e.g. excess of sebum due to hormones in skin), the bacteria/fungus detect it and there is a dysbiosis (impaired microbial balance in a particular surface). Quorum sensing is activated among them, and when cell detect that they have overcome a predetermined threshold, there is a call for releasing virulence factors, forming biofilms, causing or aiding to cause several skin diseases or disorders.

ABA is a plant hormone. It has the Systematic IUPAC name (2Z,4E)-5-[(1S)-1-hydroxy-2,6,6-trimethyl-4-oxocyclohex-2-en-1-yl]-3-methylpenta-2,4-dienoic acid. The CAS number of the racemic is 14375-45-2. The CAS number of enantiomer (+)-(S)-cis,trans-abscisic acid is 2228-72-0.

Inventors observed that the capability of ABA to inhibit quorum sensing is done at doses that are non-toxic for animal skin cells, as well as for the bacterial or fungus selves, which are preserved in order to maintain the skin microbiota. It is well known that skin microbiota helps to health preservation by avoiding, among other causes, the colonization of dangerous bacterial strains.

Furthermore, once ABA was administered to atopic skin and psoriatic skin with high signs of inflammation, a reduction of inflammatory markers was observed. The cocktail of inflammatory markers analyzed and that were reduced were related with activation of Toll-like receptors (TLR), which receptors in the skin cell membranes are activated when they are in contact with microbial patters, finally leading to activation of innate immune responses.

The observation of the action of ABA in the inhibition of biofilms supposes a new approach for the treatment of skin disorders of multiple etiologies and of high complexity such as psoriasis, atopic dermatitis and acne, in which biofilm formation takes place in minor or major grade depending on the main mechanism involved in the pathology depending on individuals. Many different mechanisms are involved in the pathology. These different mechanisms lead in addition to particular differential manifestations of the diseases, and so some drugs or actives are effective in some individuals, but they are not in others within the same categorized disease. As above exposed, these diseases are also enhanced or promoted by a dysbiosis in skin surface.

Thus, a first aspect of the invention abscisic acid, either a pharmaceutically acceptable salt or ester of abscisic acid, for use in the treatment and/or prevention of a skin disease caused by microbial biofilm formation and/or with dysbiosis of skin microbiota, said disease selected from the group consisting of psoriasis, atopic dermatitis, acne, seborrheic dermatitis, dandruff, folliculitis, contact dermatitis, topic and/or mucosal infections, rosacea and combinations thereof.

The treatment and/or prevention comprises administration of a dose causing inhibition of microbial biofilm formation. Therefore treatment and/or prevention is performed by inhibition of microbial biofilm formation.

These diseases when cursing with the microbial biofilm formation are effectively faced using ABA as quorum sensing inhibitor to inhibit the biofilm formation.

This aspect could be also the use of abscisic acid, either a pharmaceutically acceptable salt or ester of abscisic acid, for the preparation of a medicament for the prevention and/or treatment of a skin disorder or disease caused by microbial biofilm formation and/or with dysbiosis of skin microbiota, said disease selected from the group consisting of psoriasis, atopic dermatitis, acne, seborrheic dermatitis, dandruff, folliculitis, contact dermatitis, topic and/or mucosal infections, rosacea and combinations thereof. It also relates to a method for the prevention and/or treatment of the above listed skin diseases caused by microbial biofilm formation and/or with dysbiosis of skin microbiota, which comprises administering to mammals, more in particular humans, in need of such treatment an effective amount of abscisic acid, either a pharmaceutically acceptable salt or ester of abscisic acid, or a compositions comprising it.

Inventors have also developed a particular pharmaceutical composition comprising therapeutically effective amounts of abscisic acid, either a pharmaceutically acceptable salt or ester of abscisic acid, and also comprising particular plant compounds (plant cell lysates) that synergistically inhibited biofilm formation. In addition, the presence of these plant compounds provided anti-inflammatory properties, anti-oxidant properties and a regenerative action of mammal skin.

A second aspect of the invention is, therefore, a pharmaceutical composition comprising a therapeutically effective amount of abscisic acid, either a pharmaceutically acceptable salt or ester of abscisic acid, and a therapeutically effective amount of a plant cell culture selected from the group consisting of a *Morinda citrifolia* (*M. citrifolia*) cell culture lysate, *Curcuma longa* (*C. longa*) cell culture lysate,

*Olea europaea* (*O. europaea*) cell culture lysate, and combinations thereof, together with pharmaceutically or cosmetic excipients or carriers.

Although some extracts of *Morinda citrifolia*, a tropical tree known as noni, as well as its fruit juice, the oil of its seeds or of the leaves has been used in skin care regimens, its role in skin disorders caused and/or cursing with biofilm formation has never been disclosed according to the best of inventor's knowledge (see West el at., "Efficacy of a *Morinda citrifolia* Based Skin Care Regimen", Current Research Journal of Biological Sciences-2012, vol. no. 4(3), pp.: 310-314).

It is also another aspect of the invention a pharmaceutical or cosmetic composition comprising a therapeutically effective amount of abscisic acid, either a pharmaceutically acceptable salt or ester of abscisic acid, and a therapeutically effective amount of jasmonate derivative compound, together with pharmaceutically or cosmetic excipients or carriers. This pharmaceutical composition is particularly useful to face biofilm formation made by *P. aeruginosa*, as will be shown further. So that it is in particular for use of any of the skin diseases in which a *P. aeruginosa* biofilm is involved. Therefore is in particular useful for use in the prevention and/or treatment of acne and folliculitis.

Inhibition of biofilm formation by means of ABA opens also a window in other industrial fields, besides therapeutics. So that it is widely known that bacterial biofilms may be formed in other surfaces, in particular abiotic surfaces, such as in ship frame structures, in metal pipes, in conditioning air tubes (*Legionella*) or even in hospital instrument surfaces. There are widely known the problems caused by the multiresistant *S. aureus* (MRSA) in hospitals, that are difficult to be controlled and that cause many deaths each year. Also it is known that biofilms on ship structures imply an increase on fuel consumption, due to the resistance to traction the weight of the biofilm on the surface of the structure suppose. The term "abiotic surface" is to be understood as any surface which is different from a surface of a living body (i.e, skin, mucosa).

Thus, another aspect of the invention, linked with the fact that it has been discovered that ABA is able to inhibit biofilm formation, is the use of abscisic acid, either a salt or ester of abscisic acid, as inhibitor of microbial biofilm formation. Biofilm formation is avoided in particular, in biotic surfaces as well as in abiotic surfaces, as will be indicated below.

Due to the proved according to the invention effect of ABA on certain microorganisms known as being the cause of mal-odor (i.e *Corynebacterium*), another aspect of the invention is the use of abscisic acid, either a cosmetic acceptable salt or ester of abscisic acid as deodorant.

The invention also provides particular deodorant compositions that have been proved to avoid biofilm formation of the microorganism associated with the non-aesthetic mal-odour when in the skin. Thus, yet another aspect of the invention is a cosmetic deodorant composition comprising a cosmetically effective amount of abscisic acid, either a cosmetically acceptable salt or ester of abscisic acid, and a cosmetically effective amount of an ingredient selected from the group consisting of a jasmonate derivative compound, in particular, methyl jasmonate; a plant cell culture lysate; and combinations thereof, together with cosmetic excipients or carriers.

As above indicated, the invention also relates to pharmaceutical compositions comprising a therapeutically effective amount of abscisic acid, either a pharmaceutically acceptable salt or ester of abscisic acid, and a therapeutically effective amount of a jasmonate derivative compound, in particular methyl jasmonate, together with pharmaceutically or cosmetic excipients or carriers. These therapeutic combination of abscisic acid, either a pharmaceutically acceptable salt or ester of abscisic acid, and a therapeutically effective amount of a jasmonate derivative compound are useful due to the capability of inhibiting biofilm formation through inhibition of quorum sensing communication of microorganisms associated with several skin diseases cursing with the formation of such biofilm.

DETAILED DESCRIPTION OF THE INVENTION

All terms as used herein, unless otherwise stated, shall be understood in their ordinary meaning as known in the art. Other more specific definitions for certain terms as used in the present application are as set forth below and are intended to apply uniformly throughout the description and claims unless an otherwise expressly set out definition provides a broader definition.

For "skin microbiota" (also termed skin flora) is to be understood the microorganisms which reside on the skin, typically human skin. Many of them are bacteria of which there are around 1000 species upon human skin from 19 phyla. Most are found in the superficial layers of the epidermis and the upper parts of hair follicles. Skin microbiota is usually non-pathogenic, and either commensal (are not harmful to their host) or mutualistic (offer a benefit). The benefits bacteria can offer include preventing transient pathogenic organisms from colonizing the skin surface, either by competing for nutrients, secreting chemicals against them, or stimulating the skin's immune system. However, resident microbes can cause skin diseases, mainly when a dysbiosis occur, and they can even enter the blood system, creating life-threatening diseases, particularly in immunosuppressed people.

For "microbial biofilm" is to be understood any group of microorganisms in which cells stick to each other and often also to a surface. These adherent cells become embedded within a slimy extracellular matrix that is composed of extracellular polymeric substances or an exopolysaccharides (EPS). Because they have three-dimensional structure and represent a community lifestyle for microorganisms, they have been metaphorically described as "cities for microbes". Biofilms may form on living (biotic) or non-living (abiotic) surfaces and can be prevalent in natural, industrial and hospital settings. The microbial cells growing in a biofilm are physiologically distinct from planktonic cells of the same organism, which, by contrast, are single-cells that may float or swim in a liquid medium. Microbes form a biofilm in response to various different factors, which may include cellular recognition of specific or non-specific attachment sites on a surface, nutritional cues, or in some cases, by exposure of planktonic cells to sub-inhibitory concentrations of antibiotics, or the above referred quorum sensing communication system. When a cell switches to the biofilm mode of growth, it undergoes a phenotypic shift in behavior in which large suites of genes are differentially regulated.

"Skin disease cursing with microbial biofilm" or "Skin disease caused or cursing with microbial biofilm" used interchangeably, relate to skin diseases and to the different disorders or manifestations in these diseases (for example comedo, whiteheads, pustules, etc., in the properly named acne disease), all being partially or totally the result of a dysbiosis and/or of biofilm formation. Thus, the dysbiosis and/or the biofilm is present during the disease or disorder in the disease. In other words, they are diseases in which the presence of certain microorganims on skin surface is relevant for the outcome of the disease.

A "plant cell culture lysate" is a plant cell culture which has been submitted to disaggregation and disruption of the cells, by means of sonication or mechanically, via a cutting-agitator. With the disruption of the cells the content of the cytoplasm is delivered in the medium (solid or liquid), thus leading to a mixture that comprises the different components of the cell (compounds of the cytoplasm, membrane fragments and compounds from the cell previously delivered in the medium). The plant cell culture lysate can also be obtained by other means including, as a non-limitative example, freezing at very low temperature. A "plant cell culture" are plant cells derived from tissue or cells of plants, which are then cultured in a container or recipient. They have been submitted to an undifferentiation process, thus they are undifferentiated cells of the plant. The plant cell cultures are cultured plant cells aggregates (i.e calli) consisting of undifferentiated cells (mass of undifferentiated plant cells) propagated over solid culture medium containing plant hormones or in liquid culture medium containing the plant hormones (cell culture suspension).

The term "jasmonate derivative compound" or "jasmonate compound", used herewith interchangeable, encompasses compounds derived from jasmonic acid, in which one or several hydrogen atoms, namely the hydrogen atom of the hydroxyl compound, have been substituted by a $(C_1-C_3)$-alkyl radical. Examples of $(C_1-C_3)$-alkyl radical include methyl, ethyl, and propyl. Thus, some of the jasmonate derivatives compounds are methyl jasmonate, ethyl jasmonate and propyl jasmonate.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc., must also be "acceptable" in the sense of being compatible with the other ingredients of the formulation. Suitable carriers, excipients, etc. can be found in standard pharmaceutical texts, and include, as a way of example preservatives, agglutinants, humectants, emollients, and antioxidants.

The term "effective amount" as used herein, means an amount of an active agent high enough to deliver the desired benefit (either the treatment or prevention of the illness), but low enough to avoid serious side effects within the scope of medical judgment.

The compositions of the invention or the proposed use of their actives can also be cosmetic in case skin cannot be considered of suffering any disease, but that due to the presence for example of comedo or whiteheads without inflammation an unaesthetic appearance is made evident in the case of acne. In the same way, unaesthetic redness and skinny imperfections or scaling in case of psoriasis and atopic dermatitis. In this particular cases, ABA as well as any composition comprising are also used as cosmetic agents in cosmetically effective amounts and with cosmetically acceptable excipients or carriers. The term "cosmetically acceptable" or "dermatological acceptable", which is herein used interchangeably, refers to the excipients or carriers suitable for use in contact with human skin without undue toxicity, incompatibility, instability, allergic response, among others.

As above exposed, the invention relates to abscisic acid, for use in the treatment and/or prevention of a skin disease caused and cursing with microbial biofilm formation and/or with dysbiosis of skin microbiota. In particular treatment and/or prevention comprises administration of a dose causing inhibition of microbial biofilm formation. Therefore treatment and/or prevention is performed by inhibition of microbial biofilm formation.

In a particular embodiment of the first aspect, the microbial biofilm is formed by a microorganism selected from the group consisting of *Propionibacterium acnes, Staphylococcus aureus, Pseudomonas aeruginosa, Malassezia furfur, Streptococcus pyogenes, E. coli, Candida albicans, Corynebacterium, Epidermophytum floccosum, Streptococcus mutans, Firmicutes, Proteobacteria* and combinations thereof. More in particular the biofilm is formed by *Propionibacterium acnes, Staphylococcus aureus, Pseudomonas aeruginosa, Malassezia furfur Streptococcus pyogenes, Candida albicans, Corynebacterium striatum, Epidermophytum floccosum, Streptococcus mutans* and combinations thereof. Even more in particular it is formed by *Propionibacterium acnes*, and/or *Staphylococcus aureus*.

Thus, invention relates to abscisic acid, for use in the treatment and/or prevention of a skin disease caused and cursing with microbial biofilm formation and/or with dysbiosis of skin microbiota, the microbial biofilm being formed by a microorganism selected from species of the genera *Propionibacterium, Staphylococcus, Pseudomonas, Malassezia, Streptococcus, Escherichia, Candida, Corynebacterium, Epidermophytum, Firmicutes, Proteobacteria* and combinations thereof.

In another particular embodiment, the dysbiosis of skin microbiota is an imbalance of the bacterial skin population of *Propionibacterium acnes, Staphylococcus aureus*, and *Staphylococcus epidermidis*. This imbalance results in the increase of the population of *Propionibacterium acnes*, and/or *Staphylococcus aureus* in relation with a skin without any of the skin disorders; and a decrease of the population of *Staphylococcus epidermidis*. Population of the bacteria is determined as colony forming units (CFU) per surface area.

As will be shown below, abscisic acid or a pharmaceutical composition comprising it was able to re-balance the dysbiosis in patients suffering from acne. Thus, in another particular embodiment of the first aspect of the invention, the skin disorder caused and cursing with microbial biofilm formation and/or with dysbiosis of skin microbiota is acne. More in particular is acne (synonym of acne vulgaris) selected from the group consisting of inflammatory acne, non-inflammatory acne, and combinations thereof. Non-inflammatory acne includes blackheads and whiteheads. These normally don't cause swelling. They also respond relatively well to over-the-counter (OTC) treatments. Pimples that are red and swollen are referred to as inflammatory acne. Although sebum and dead skin cells contribute to inflammatory acne, bacteria can also play a role in clogging up pores. Bacteria can cause an infection deep beneath the skin's surface. This may result in painful acne spots that are hard to get rid of.

As indicated, many can be the mechanisms and causes leading to acne manifestation. So that, it is widely accepted that the hormonal status or changes of the individual is important, but hormonal profile during adolescent and leading to have a prone to acne skin is different than the hormonal profile observed in women in menopause or in depressed individuals, that can also lead to acne manifestation. Although in acne is widely accepted that there is a dysbiosis of skin microbiota, it is also widely accepted that there are different grades of acne.

The herewith proposed used in acne of ABA and of compositions comprising, it is in particular to face acne manifestations in which the formation of the biofilm is of relevance. In addition, since quorum sensing is inhibited the proposed use is in particular for initial manifestations of acne, to avoid the complications of inflammation once the biofilm is established and the anaerobic behavior promotes bacterial growth. In addition, when ABA in the pharmaceutical composition is accompanied with a plant cell culture lysate with anti-inflammatory, antioxidant and regenerative properties, the composition faces several of the aspects concurring in the skin disease.

In addition using ABA to reduce biofilm formation in acne is advantageous since it does not imply secondary effect, contrary to current acne treatments. Current treatments used for acne (antibiotics, oil removers, etc.) do imply as secondary effects that immune barrier can be jeopardized, and in particular that the skin barrier formed by keratinocytes is impaired (keratolytic effect).

In another particular embodiment of the first aspect, the disease is psoriasis. As illustrated below, pharmaceutical compositions comprising ABA were able to inhibit biofilm formation of *Propionibacterium acnes, Staphylococcus aureus*, but also of the fungus *Malazzezia furfur*, the latter being involved in psoriasis and considered one of the actors in the inflammatory process detected in this complex skin disorder.

Yet in another particular embodiment of the first aspect, the skin disease is atopic dermatitis. This disease is conveniently treated with abscisic acid when *S. aureus* population is increased in patient's skin. Other film forming microorganisms involved in atopic dermatitis include *S. epidermidis* and *Malassezia*. (see. Powers et al., supra).

Abscisic acid according to the present invention can be used in its acid form, but also in form of any pharmaceutically acceptable salts or pharmaceutically acceptable esters of the acid. Particular salts are salts of alkaline metals, such as sodium salt. Particular esters include glucose ester ((+/−)-abscisic acid beta-D glucose ester), $C_1$-$C_3$ alkyl esters, in particular methyl ester. In a particular embodiment according to the invention, abscisic acid is in form of acid, the enantiomer (+)-(S)-cis,trans-abscisic acid (synonym of (S)-5-(1-hydroxy-2,6,6-trimethyl-4-oxo-2-cyclohexen-1-yl)-3-methyl-(2Z,4E)-pentadienoic acid). In another particular embodiment is the racemic (2Z,4E)-5-[(1S)-1-hydroxy-2,6,6-trimethyl-4-oxocyclohex-2-en-1-yl]-3-methylpenta-2,4-dienoic acid. For "$C_1$-$C_3$ alkyl" is to be understood methyl, ethyl, n-prolyl and isopropyl.

In another particular embodiment of the first aspect, abscisic acid is in form of a pharmaceutical composition comprising a therapeutic effective amount of abscisic acid, or either a pharmaceutically acceptable salt or ester of abscisic acid, together with pharmaceutically excipients or carriers.

In another particular embodiment, said abscisic acid is for use as defined above and wherein the treatment comprises administering abscisic acid at a therapeutically effective dose causing inhibition of microbial biofilm formation by means of the modulation of microbial quorum sensing communication. Modulation of the quorum sensing means that said quorum sensing is inhibited or dismissed in such a way that microbial cannot communicate in an effective way to produce biofilms.

A second aspect of the invention is a particular pharmaceutical composition comprising a therapeutically effective amount of abscisic acid, either a pharmaceutically acceptable salt or ester of abscisic acid, and a therapeutically effective amount of a plant cell culture selected from the group consisting of a *Morinda citrifolia* cell culture lysate, *Curcuma longa* cell culture lysate, *Olea europaea* cell culture lysate, and combinations thereof, together with pharmaceutically or cosmetic excipients or carriers.

In a particular embodiment of the second aspect, optionally in combination with any of the embodiment above or below, the pharmaceutical composition comprises a therapeutically effective amount of a plant cell culture selected from the group consisting of a *Morinda citrifolia* cell culture lysate, *Olea europaea* cell culture lysate, and combinations thereof.

In a particular embodiment of the second aspect, optionally in combination with any of the embodiment above or below, the percentage by weight of abscisic acid, either of a pharmaceutically acceptable salt or ester of abscisic acid is from $10\times10^{-4}$% to $60\times10^{-4}$% in relation with the total weight of the composition. In the particular case when the composition is in form of a liquid composition, the amount of abscisic acid, either of a pharmaceutically acceptable salt or ester of abscisic acid, is from $15\times10^{-4}$% to $45\times10^{-4}$%. Even more in particular is from $15\times10^{-4}$% to $30\times10^{-4}$%. If not indicated to the contrary, percentages are defined as percentages by weight, also represented by w/w, in relation with the total weight of the compositions.

In another particular embodiment of this second aspect, the pharmaceutical composition comprises a plant cell culture lysate of *Morinda citrifolia* (or *Morinda citrifolia* cell culture lysate). In a more particular embodiment the percentage by weight of the cell lysate of a plant cell culture of *Morinda citrifolia* is from 2% to 50% in relation with the total weight of the pharmaceutical composition. More in particular from 5% to 30% w/w. Even more in particular is from 5% to 15% w/w.

In another particular embodiment of this second aspect, the pharmaceutical composition comprises a plant cell culture lysate of *Olea europaea.*

Several cell culture lysates of *Morinda citrifolia* and/or of *Olea europaea* can be used. In a particular embodiment of the invention, the lysate of a plant cell culture of *Morinda citrifolia* comprises polyphenols, anthraquinones, terpenoids, flavonoids and phytosterols. In a particular embodiment the plant cell culture lysate of *Morinda citrifolia* comprises from 10 to 2000 ppm of polyphenols, more in particular from 40 to 1000 ppm, even more in particular from 100 to 500 ppm of polyphenols; and from 10 to 1000 ppm of anthraquinones, more in particular from 50 to 500 ppm, and even more in particular from 100 to 200 ppm of anthraquinones. The amounts of polyphenols, terpenoids and flavonoids are determined in the cell culture lysates using any colorimetric method. Anthraquinones by HPLC, and phytosterols using thin layer chromatography (TLC).

Polyphenols are a structural class of mainly natural, but also synthetic or semisynthetic, organic chemicals characterized by the presence of large multiples of phenol structural units. Anthraquinone, also called anthracenedione or dioxoanthracene, is an aromatic organic compound with formula $C_{14}H_8O_2$. Several isomers are possible, each of which can be viewed as a quinone derivative. Terpenoids (also named isoprenoids) are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Examples of isoprenoids in plants include abscisic acid. Flavonoids are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Plant flavonoids are classified according to their chemical structure into the following subgroups: Anthoxanthins (including flavones, flavonols), flavanones, flavanolols, flavans and anthocyanidins. Phytosterols which encompass plant sterols and stanols, are phytosteroids, similar to cholesterol, which occur in plants and vary only in carbon side chains and/or presence or absence of a double bond.

In yet a more particular embodiment, the plant cell culture lysate of *Morinda citrifolia* with the above-referred composition is obtainable by a method comprising:

a) cultivating plant cells *Morinda citrifolia* in a suitable growing medium, said growing medium comprising plant hormones selected from auxins, cytokines and mixtures thereof, and maintaning the culture by sub-culturing from each 14 to 21 days, in particular with an inoculum of ¼ of the growing medium;

b) adding one volume of culture of step a), previously grown during a period from 14 to 21 days, to three volumes of a culture medium comprising plant hormones and methyljasmonate, and maintaing the culture from 10 to 18 days; and c) lysing the plant cell culture to obtain a plant cell lysate, in particular by mechanical disruption, french press and/or sonication.

Particular growing medium for cultivating plant cells *Morinda citrifolia* is the Murashige & Skoog (MS) medium. This medium is then supplemented with plant hormones or with methyljasmonate as elicitator.

In the same way, in a particular embodiment of the invention, the lysate of a plant cell culture of *Olea europaea* comprises polyphenols in a concentration from 1000 to 10000 mg/l, more in particular from 2000 to 5000 mg/l, and even more in particular from 3500 to 4500 mg/l of cell culture, determined by means of a colorimetric method.

In yet a more particular embodiment, the plant cell culture lysate of *Olea europaea* with the above-referred composition is obtainable by a method comprising:

a) cultivating plant cells *Olea europaea* in a suitable growing medium, said growing medium comprising plant hormones selected from auxins, cytokines and mixtures thereof, and maintaining the culture by sub-culturing from each 14 to 21 days, in particular with an inoculum of ¼ of the growing medium;

b) adding one volume of culture of step a), previously grown during a period from 14 to 21 days, to two volumes of a culture medium comprising plant hormones and methyljasmonate, and maintaining the culture from 10 to 18 days; and c) lysing the plant cell culture to obtain a plant cell lysate, in particular by mechanical disruption, french press and/or sonication.

Particular growing medium for cultivating plant cells of *Olea europaea* is the Rugini Olive Medium. This medium is then supplemented with plant hormones or with methyl jasmonate as elicitator.

In another particular embodiment, the *Olea europaea* is selected from *Olea europea, Olea europea* var. *Sylvestris* (wild olive tree) and mixtures thereof. In particular, it is *Olea europea* var. *Sylvestris.*

Inventors have determined that particular ratios of the two active-ABA and cell lysate of *Morinda citrifolia* and/or of *Oliva europaea* were highly active in avoiding biofilm formation of several bacterial species. Therefore, in another particular embodiment, the pharmaceutical composition comprises abscisic acid, either of a pharmaceutically acceptable salt or ester of abscisic acid, and a plant cell culture lysate of *Morinda citrifolia.*

In a more particular embodiment, the pharmaceutical composition comprises a percentage by weight in the composition of the cell culture lysate of *Morinda citrifolia* from 2% to 50% and the abscisic acid is from $10\times10^{-4}\%$ to $60\times10^{-4}\%$, in relation with the total weight of the composition. More in particular, they are from 5% to 50% w/w of *Morinda citrifolia* cell lysate and from $15\times10^{-4}\%$ to $45\times10^{-4}\%$ of abscisic acid. In another more particular embodiment, they are from 5% to 15% of cell lysate and from $15\times10^{-4}\%$ to $45\times10^{-4}\%$ of abscisic acid.

Another particular embodiment of the pharmaceutical composition according to the second aspect, it comprises a percentage by weight in the composition of the cell culture lysate of *Morinda citrifolia* from 25% to 50%, more in particular 30%, and from $10\times10^{-4}\%$ to $60\times10^{-4}\%$, in particular $30\times10^{-4}\%$ of abscisic acid, and wherein the pharmaceutical excipients or carriers comprise glycerine and preservatives in an amount to reach 100% by weight of the composition.

In yet a more particular embodiment, this pharmaceutical composition comprising from 25% to 50%, more in particular 30% of *Morinda citrifolia* cell lysate, and from $10\times10^{-4}\%$ to $60\times10^{-4}\%$, in particular $30\times10^{-4}\%$ of abscisic acid, glycerine and preservatives is used as a mixture of active ingredients in further derived pharmaceutical compositions, in form of creams, gels, unguents, oils, sprays and emulsions. In these derived pharmaceutical compositions, particular amounts of the composition defined by the mixture of glycerine, preservatives, *Morinda citrifolia* cell lysate and abscisic acid are from 0.5% to 5.0% by weight of the total weight of the derived composition. More in particular it is in an amount from 0.5% to 2.0% by weight of the total weight of the derived composition (i.e. cream, gel, unguent, etc.).

These concentrations of abscisic acid had a bacteriostatic and fungistatic effect and so also inhibited biofilm formation. In addition, these amounts where non-toxic for skin cells and re-equilibrated the population of *S. epidermidis*, which is considered a healthy microorganism for skin.

Thus, the invention also relates to the use of ABA, either a pharmaceutically acceptable salt or ester of ABA as a bacteriostatic or as a fungistatic agent.

High concentrations of abscisic acid have been also analyzed and they had a bactericide or fungicide effect. The final effect of the molecule on bacterial populations will depend on what is desired and if a more aggressive treatment is recommended. Thus, the invention also relates ABA, either a pharmaceutically acceptable salt or ester as a bactericide agent or as a fungicide agent. Nonetheless, in the particular case of bacteria, inventors do propose using bacteriostatic doses rather than bactericide doses, when possible, in order to avoid the secondary problems of inducing resistance by bacteria with bactericides.

Indeed, one of the main goals of the proposed used of ABA and of the compositions of the invention is that they did not kill the microorganism on the skin surface, but maintain them in an appropriate level (density in cfu per area) to take profit of them as symbiotic organisms controlling they do not become virulent or prejudicial. This is done by hacking (inhibiting) the communication between microbial cells, so that blocking quorum sensing. This blocking makes microbial cell cannot form biofilms, which biofilms are phenotypic presentations of the microorganisms resistant to antibiotics and also promoting inflammation of skin. By means of this mode of action, in which ABA acts as bacterostatic or fungistatic and biofilm inhibitor, inflammation is avoided because there are no killed bacterial cells. Killed by any bactericide or fungicide, the cells of bacteria or fungus could still stimulate immune cells present in skin if they reached high levels on the surface and/or if due to disaggregation of the same they expose inflammatory antigens, worsening the skin disorder, instead of solving it.

Another aspect of the invention is a pharmaceutical composition comprising a therapeutically effective amount of abscisic acid, either a pharmaceutically acceptable salt or ester of abscisic acid, and a therapeutically effective amount of jasmonate derivative compound, together with pharmaceutically or cosmetic excipients or carriers. In a particular embodiment of this combination including ABA and a jasmonate derivative, said jasmonate derivative is selected from methyl jasmonate, ethyl jasmonate and propyl jasmonate. More in particular is methyl jasmonate.

Also due to the proved effect of ABA on certain microorganisms associated with tooth decay (i.e. *S. mutans* associated with dental caries), the invention also relates to the use of ABA as oral care agent, optionally accompanied by methyl jasmonate or any other jasmonate derivative compound. Tooth decay is more related with disease than a cosmetic or non-aesthetic issue, although it has also an impact on the appearance of oral cavity due to the darkness effect. Therefore, in a particular embodiment the pharmaceutical or cosmetic composition according to the invention is a composition for oral care, and it comprises the effective amounts to prevent and/or to avoid progression of tooth decay. In a particular embodiment, the pharmaceutical or cosmetic compositions for oral case comprise from ABA in a concentration from 45 μg/ml to 60 μg/ml in a tested media, and methyl jasmonate from 15 to μg/ml to 60 μg/ml in the composition.

As will be proved in the Examples, ABA alone or in combination with jasmonate compounds, or with cell culture lysates (in particular of *Morinda citrifolia*) were able to act as fungistatic and fungicides when tested in front of *Epidermophytum floccosum*. Therefore, the invention also relates to the use of these compounds in combination as anti-fungus agent or in fungus skin and nail infections in humans, in particular mycodermatitis. Therefore, in a particular embodiment the pharmaceutical or cosmetic composition according to the invention is an anti-fungal composition, and it comprises the in a more particular embodiment, ABA in a concentration from 30 μg/ml to 60 μg/ml in a tested media or compositions, and methyl jasmonate from 15 to μg/ml to 35 μg/ml. In another particular embodiment, the anti-fungal composition comprises ABA in a concentration from 30 μg/ml to 60 μg/ml and *Morinda citrifolia* cell culture lysate from 20% to 30% in relation with the total weight of the composition.

The pharmaceutical composition of the invention is also effective with other fungus, namely *Candida albicans* and *Malassezia furfur*. Thus, the invention also relates to particular pharmaceutical anti-fungic compositions for *C. albicans* infections. *C. albicans* is associated with gynecological diseases. In a particular embodiment of the pharmaceutical compositions for *C. albicans*, ABA is in a concentration from 45 μg/ml to 60 μg/ml. In another particular embodiment, the composition further comprises methyl jasmonate in a concentration from 35 μg/ml to 40 μg/ml. These compositions are for use in several infections of the vagina and anus. Besides, these compositions are also for use in psoriasis, since *Candida albicans* and *Malassezia furfur* are associated with these diseases.

Also associated with psoriasis is also *Streptococcus pyogenes*, another microorganism in which the pharmaceutical compositions of the invention comprising ABA are effective. In a particular embodiment, the compositions for psoriasis comprises ABA from 30 μg/ml to 45 μg/ml, and *Morinda citrifolia* cell culture lysate from 20% to 25% in relation with the total weight of the composition.

The pharmaceutical composition of the invention is also effective in skin diseases cursing with biofilm formation of *Staphylococcus aureus* that has been associated with atopic dermatitis. In a particular embodiment of the pharmaceutical composition for use in *S. aureus* associated skin diseases, it comprises ABA from 30 μg/ml to 60 μg/ml, and a jasmonate derivative compound, in particular methyl jasmonate, from 35 μg/ml to 60 μg/ml in the composition.

The invention also relates to the use of abscisic acid, either a salt or ester of abscisic acid, as inhibitor of microbial biofilm formation. Microbial biofilm formation is inhibited in abiotic surfaces, as well as in biotic surfaces as will be illustrated below.

In particular it is illustrated for mammal skin surfaces, in particular human, wherein the microbial biofilm is formed by a microorganism selected from the group consisting of *Propionibacterium acnes, Staphylococcus aureus, Pseudomonas aeruginosa, Malassezia furfur, Streptococcus pyogenes, Candida albicans, Corynebacterium striatum, Epidermophytum floccosum, Streptococcus mutans* and combinations thereof. Nonetheless, the use as inhibitor of the quorum sensing and further of the formation of microbial biofilms is also for other type of biotic (living) surfaces, in particular selected from eye surface, mucosal surfaces including mouth, urethra, anus surface, vaginal surface, nasal holes and ear (external and internal) surface. Indeed, the term "topic and/or mucosal infections" according to this description relates to surfaces including skin as well as mucosa (mucous membrane) continuous with the skin at various body openings such as the eyes, ears, inside the nose, inside the mouth, lip, vagina, the urethral opening and the anus. Some mucous membranes secrete mucus, a thick protective fluid. The function of the membrane is to stop pathogens and dirt from entering the body and to prevent bodily tissues from becoming dehydrated. Thus, when referring to mucous membrane of the vagina, ABA or a composition comprising ABA and a plant cell culture lysate as above disclosed are also for use in the gynecological area.

Other particular surfaces are surfaces of ship structures that accumulate biofilm along time, surfaces of pipes, surfaces of air conditioning devices (tubes), glass and borosilicate surfaces (coupons), and surfaces of medical instruments. Thus, the invention also encompasses the non-therapeutic use of abscisic acid, either a salt or ester of abscisic acid, as inhibitor of microbial biofilm formation.

Proposed ABA for use in the treatment of skin diseases cursing with microbial biofilm formation and/or with dysbiosis of skin microbiota, as well as the use of this ABA in abiotic surfaces results from the unexpected effect observed by inventors of this acid as inhibitor of microbial biofilm formation.

Due to the effect of ABA on certain microorganism known being the cause of mal-odor (i.e *Corynebacterium*), another aspect of the invention is the use of abscisic acid, either a cosmetic acceptable salt or ester of abscisic acid as deodorant.

As indicated before, the invention also relates to the use of abscisic acid, either a cosmetic acceptable salt or ester of abscisic acid as deodorant, and to deodorant cosmetic compositions.

In a particular embodiment of the cosmetic compositions, they comprise besides ABA, a salt or ester thereof, an ingredient selected from a *Morinda citrifolia* cell culture lysate, *Olea europaea* cell culture lysate, a *Curcuma longa* cell culture lysate, and combinations thereof. In another particular embodiment, the cell lysate is a *Morinda citrifolia* cell culture lysate. In another particular embodiment, the cell lysate is an *Olea europaea* cell culture lysate. In another particular embodiment, the cell lysate is a *Curcuma longa* cell culture lysate.

In another particular embodiment, the cosmetic deodorant compositions comprise ABA, a salt or ester thereof, and methyl jasmonate in cosmetically effective amounts.

These cosmetic deodorant compositions are, in another particular embodiment selected from creams, gels, unguents, oils, sprays and emulsions.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

Bacteriostatic Effect of ABA and Plant Cell Culture Lysates of *M. Citrifolia*

In this example several concentrations of ABA ((+)-(S)-cis,trans-abscisic acid (synonym of (S)-5-(1-hydroxy-2,6,6-trimethyl-4-oxo-2-cyclohexen-1-yl)-3-methyl-(2Z,4E)-pentadienoic acid)) (60 μg/ml, 30 μg/ml, 15 μg/ml, 5 μg/ml) were tested in a culture of *P. acnes*. Different amounts of the *Morinda citrifolia* cell lysate disclosed in Example 6 below were also tested in the same conditions (60%, 30%, 10%, 1%, 0.5%) by weight of cell lysate in the *P. acnes* culture. Next table shows the colony forming units (cfu) detected at inoculum day and at 24 hours later without any treatment (*P. acnes* control) and with the treatment with ABA or with the *Morinda citrifolia* cell lysate. The same protocol was followed with a culture of *S. aureus* and with a culture of *M. furfur*. Data are shown in next Tables 1.1 to 1.6, where bacteriostatic and bactericide concentrations are listed. Underlined concentrations are the considered bacteriostatic or fungistatic amounts and that they avoid biofilm formation.

TABLE 1.1

| | Inoc. Day | *P. acnes* | Concentration of tested ABA (μg/ml) | |
|---|---|---|---|---|
| | *P. acnes* | control | 60(*) | 30 |
| CFU | 320000 | 1490000 | 100000 | 158001 |

(*)concentration considered bactericide

TABLE 1.2

| | Inoc. Day | *P. acnes* | Concentration of tested *Morinda citrifolia* cell lysate (% by weight in the culture) | |
|---|---|---|---|---|
| | *P. acnes* | control | 60(*) | 30 |
| CFU | 320000 | 1490000 | 156000 | 280500 |

(*)concentration considered bactericide

TABLE 1.3

| | Inoc. Day *S. aureus* | *S. aureus* control | Concentration of tested ABA (μg/ml) 60 |
|---|---|---|---|
| CFU | 520000 | 3310000 | 585000 |

TABLE 1.4

| | Inoc. Day | *S. aureus* | Concentration of tested *Morinda citrifolia* cell lysate (% by weight in the culture) | | |
|---|---|---|---|---|---|
| | *S. aureus* | control | 60 (*) | 30 (*) | 10 |
| CFU | 520000 | 3310000 | 39900 | 60000 | 495500 |

(*) concentration considered bactericide

TABLE 1.5

| | Inoc. Day | *M. furfur* | Concentration of tested ABA (μg/ml) | |
|---|---|---|---|---|
| | *M. furfur* | control | 60(*) | 30 |
| CFU | 420000 | 1470000 | 256000 | 529000 |

(*)concentration considered fungicide

TABLE 1.6.

| | Inoc. Day | *M. furfur* | Concentration of tested *Morinda citrifolia* cell lysate (% by weight in the culture) | |
|---|---|---|---|---|
| | *M. furfur* | control | 60 | 30 |
| CFU | 420000 | 1470000 | 253000 | 191000 |

As can be deduced from these tables 1.1-1.6, both tested compounds (ABA and *Morinda citrifolia* cell lysate) maintained the cfu of the microorganisma under control.

*Morinda citrifolia* cell lysate contained a cocktail of compounds (also traces of ABA) that do also promoted the inhibition of quorum sensing and biofilm formation.

*S. aureus, P. aeruginosa, P. acnes*, and *M. furfur* subcultures were carried out from the stock by streaking onto determined medium and incubated according to the conditions specified for each of the microorganisms according to standard procedures and as indicated below:

| Microorganism | Type Culture Collection | Growth conditions | Growth medium |
|---|---|---|---|
| *Staphylococcus aureus* | ATCC 6538 (commercially available) | 37° C./24 h aerobic | Nutrient Agar/Broth |
| *Pseudomonas aeruginosa* | CECT 116 (commercially available) | 37° C./24 h aerobic | Nutrient Agar/Broth |
| *Propionibacterium acnes* | DSM 1897 (commercially available) | 37° C./48 h anaerobic | Reinforced Clostridial Agar/Broth |
| *Malassezia furfur* | ATCC 14521 (commercially available) | 30° C./48 h aerobic | m-Dixon Agar/Broth |

Further it was tested a composition comprising 30% of *Morinda citrifolia* cell lysate and $30\times10^{-4}$% of abscisic acid ((+)-(S)-cis,trans-abscisic acid), glycerine and preservatives (q.s. 100%) in cultures of *P. acnes, S. aureus, P. aeruginosa* and *M. furfur*. The composition was used in the microbial culture at 5% and at 10% of the culture.

In all the microbial cultures tested following the above exposed conditions, the composition comprising 30% of *Morinda citrifolia* cell lysate and $30\times10^{-4}$% of abscisic acid was able to maintain the cfu at the level of inoculation. Thus, it had a bacteriostatic/fungistatic effect and it avoided biofilm formation (between 100000 cfu and 1000000 cfu).

In a parallel assay, it was tested if these effects were effectively due to the inhibition or quenching of the quormones (AIs), and thus if it inhibited the quorum sensing of the microbial. For this, LUX-S gene expression was analysed in a *P. acnes* culture by RT-PCR, using specific Taqman probes and quantifying the gene using Agilent platform Bioanalyzer 2100 (expression levels were normalized with expression of the 16S ribosomal gene). A composition comprising 30% of *Morinda citrifolia* cell lysate and $30\times10^{-4}$% of abscisic acid (at 5% w/w or 15% w/w in the culture) was able to inhibit LUX-S gene expression up to −89% in *P. acnes*. This meant that the composition had the ability to interfere very specifically in the quorum sensing of *P. acnes* by inhibition of the synthesis of quormones.

In addition, the same composition comprising 30% of *Morinda citrifolia* cell lysate and $30\times10^{-4}$% of abscisic acid was tested in an assay of modulation of microbial-keratinocyte interaction and emission of Interleukin-1α (IL-1α), a marker of interaction of keratinocytes with fragments of *P. acnes*. Keratinocytes were treated with the composition at several culture concentrations (0.01%, 0.1% and 2%). Activation capacity of Toll-like receptor 2 (TRL-2) by means of a *P. acnes* cell lysate, was tested by analyzing the released levels of IL-1α (PCR) from this keratinocytes culture. Assayed compositions of *Morinda citrifolia* cell lysate and abscisic acid at all tested concentrations were able to decrease the levels of IL-1α up to −120% compared to a control without treatment. This allowed concluding that the compositions had the ability to interfere in the microbial-keratinocyte interaction by blocking TLR-2.

Example 2

Bacteriostatic Effect of ABA and Plant Cell Culture Lysates of *Olea Europaea*

Following the same scheme as in Example 1, different amounts of the *Olea europaea* cell lysate (60%, 30%, 10%, 1%, 0.5%, 0.1%) disclosed in Example 6 below, were also tested over a *P. acnes* culture, a *S. aureus* culture, a *P. aeruginosa* culture and with a culture of *M. furfur*. Data are listed in Tables 2.1 to 2.4

TABLE 2.1

| | Inoc. Day | *P. acnes* | Concentration of tested *Olea europaea* cell lysate (% by weight in the culture) | |
|---|---|---|---|---|
| | *P. acnes* | control | 60(*) | 30 |
| CFU | 320000 | 1490000 | 193000 | 420000 |

TABLE 2.2

| | Inoc. Day | *S. aureus* | Concentration of tested *Olea europaea* cell lysate (% by weight in the culture) | |
|---|---|---|---|---|
| | *S. aureus* | control | 60 (*) | 30 |
| CFU | 520000 | 3310000 | 192150 | 475500 |

TABLE 2.3

| | Inoc. Day *P. aeruginosa* | *P. aeruginosa* control | Concentration of tested *Olea europaea* cell lysate (% by weight in the culture) 60 |
|---|---|---|---|
| CFU | 243000 | 1655000 | 247000 |

TABLE 2.4

| | Inoc. Day | *M. furfur* | Concentration of tested *Olea europaea* cell lysate (% by weight in the culture) | |
|---|---|---|---|---|
| | *M. furfur* | control | 60 (*) | 30 |
| CFU | 420000 | 1470000 | 160000 | 480000 |

Example 3

Inhibition of Biofilm Formation on Coupons. Synergic Effect

In order to test the inhibitory effect of biofilm formation, particular compositions comprising ABA ((+)-(S)-cis,trans-abscisic acid) and cell lysate of a plant cell culture of *Morinda citrifolia* were also tested in an assay on glass coupons that also served as example of biofilm formation on abiotic surfaces.

Generation of representative biofilms on borosilicate glass coupons (12.7 mm diameter and a thickness of 3.7 mm) by immersion of the coupons in a suspension of each microorganism with culture medium and the compounds of interest was tested. Evaluation of the antibiofilm properties and study of adhesion, growth and viability of biofilms on the coupons was analyzed by fluorescence staining technique and visualization of live/dead microbial was done by Laser Scanning Confocal Microscopy. The sampling and analysis of coupons to determine biofilm population density was recorded as colony-forming units (cfu) per coupon. In parallel, planktonic cells quantification in suspension was also determined.

The biofilm development can be roughly divided into three stages: 1) initial attachment, in which a reversible surface attachment by planktonic, free-swimming microbial, onto a surface suitable for growth takes place; 2) biofilm formation, in which intercellular adhesion and accumulation of multi-layered cell clusters occurs, extracellular polymer production and generation of slime glycocalix takes place, and intercellular communication through quorum sensing occurs to mature the biofilm; and 3) biofilm persistence, detachment of cell clusters, when biofilms disperse and microbial clusters re-enter in planktonic state to colonize other surfaces.

The suspension of each microorganism to generate biofilm were prepared by adjusting the number of microbial cells to an average value between 1.5-5×$10^7$ cfu/ml in each specific broth medium.

| Microorganism | Type Culture Collection | Biofilm generation conditions | Medium |
|---|---|---|---|
| *Staphylococcus aureus* | ATCC 6538 (commercially available) | 37° C./5 days aerobic | Nutrient Broth |

-continued

| Microorganism | Type Culture Collection | Biofilm generation conditions | Medium |
|---|---|---|---|
| *Propionibacterium acnes* | DSM 1897 (commercially available) | 37° C./5 days anaerobic | Reinforced Clostridial Broth |
| *Malassezia furfur* | ATCC 14521 (commercially available) | 30° C./5 days aerobic | m-Dixon Broth |

The tested combinations of ABA and *Morinda citrifolia* cell lysate were as follows:

TABLE 3

| Combinations tested in *P. acnes* *Propionibacterium acnes* | | | | | |
|---|---|---|---|---|---|
| ABA (μg/ml in the *P. acnes* culture) | 30 | 30 | 15 | 45 | 60 |
| *Morinda citrifolia* cell lysate (% by weight in the *P. acnes* culture) | 15 | 5 | 10 | 5 | 2 |

TABLE 4

| *P. acnes* biofilms on coupons | | | | | | | |
|---|---|---|---|---|---|---|---|
| | Inoc. Day *P. acnes* (at 0 hours) | *P. acnes* control (after 5 days) | Concentration of tested ABA (μg/ml)/cell lysate (%) and CFU after 5 days of culture | | | | |
| | | | 30/15 | 30/5 | 15/10 | 45/5 | 60/2 |
| CFU | 52000000 | 207500000 | 200 | 200 | 200 | 200 | 30500 |

All tested combinations had biofilm inhibitory capacity. The complementary data on planktonic cells are listed in next Table:

TABLE 5

| *P. acnes* in suspension | | | | | | | |
|---|---|---|---|---|---|---|---|
| | Inoc. Day *P. acnes* (at 0 hours) | *P. acnes* control (after 5 days) | Concentration of tested ABA (μg/ml)/cell lysate (%) and CFU after 5 days of culture | | | | |
| | | | 30/15 | 30/5 | 15/10 | 45/5 | 60/2 |
| CFU | 52000000 | 687000000 | 61600000 | 61850000 | 52716667 | 69500000 | 63000000 |

These data confirm again that the compositions have bacteriostatic effect. So that, that the bacterial cells were viable cells and where not killed.

TABLE 6

| Combinations tested in *S. aureus* *Staphylococcus aureus* | | | | | |
|---|---|---|---|---|---|
| ABA (μg/ml in the *P. acnes* culture) | 30 | 30 | 15 | 15 | 15 |
| *Morinda citrifolia* cell lysate (% by weight in the *P. acnes* culture) | 10 | 5 | 30 | 10 | 5 |

TABLE 7

| *S. aureus* biofilms on coupons | | | | | | | |
|---|---|---|---|---|---|---|---|
| | Inoc. Day *S. aureus* (at 0 hours) | *S. aureus* control (after 5 days) | Concentration of tested ABA (μg/ml)/cell lysate (%) and CFU after 5 days of culture | | | | |
| | | | 30/10 | 30/5 | 15/30 | 15/10 | 15/5 |
| CFU | 32000000 | 2975000000 | 352500 | 480000 | 337500 | 568500 | 592750 |

All tested combinations had biofilm inhibitory capacity. The complementary data on planktonic cells are listed in next Table.

TABLE 8

| *S. aureus* in suspension | | | | | | | |
|---|---|---|---|---|---|---|---|
| | Inoc. Day *S. aureus* (at 0 hours) | *S. aureus* control (after 5 days) | Concentration of tested ABA (μg/ml)/cell lysate (%) and CFU after 5 days of culture | | | | |
| | | | 30/10 | 30/5 | 15/30 | 15/10 | 15/5 |
| CFU | 32000000 | 297500000 | 18575000 | 14937500 | 18050000 | 33925000 | 28225000 |

These data confirm again that the compositions have bacteriostatic effect. Again, bacterial cells were viable cells.

For the determination of biofilm populations the microbial population adhered to the coupon surface were quantified by dilution and plating after biofilm disaggregation process by sonication and vortex cycles. The planktonic cells (suspension) were determined by dilution and plating. The controls were, respectively the cells on coupons or in suspension after 5 days without any treatment.

Example 4

Effect of ABA in Skin Biopsies of Atopic Dermatitis (AD) and Psoriasis (PSO)

In skin biopsies of patients with plaque psoriasis and from patients with atopic dermatitis, it was determined the expression of several inflammatory markers (Interleukin 23A (IL-23A), C-X-C motif chemokine 10 (CXCL10), Interleukin 8 (IL-8), Interleukin 20 (IL-20), Intercellular Adhesion Molecule 1 (ICAM-1), LNC2, DEF-4, Keratin 16 (K-16), Interferon gamma (IFNg) and Interleukin 17A (IL-17A) using commercially available PCR tools for their determinations (RT-PCR by RNeasy Fibrous Tissue Mini kit and cDNA Archive kit, Sigma, ABlprism 7900HT and TaqMan probes). As a control, dexamethasone was used. Results are in Table 9(A-B) and Table 10(A-B) below.

Full-thickness lesional skin biopsies from untreated atopic dermatitis and psoriasis patients were incubated in KBM medium supplemented with $Ca_2Cl$ for 8 days at 37° C., conditions that preserve human skin lesional in vitro. The different culture conditions were media, ABA (2 μL/ml (+)-(S)-cis,trans-abscisic acid). Medium was changed every 2-3 days. After incubation biopsies were cryopreserved in OCT at −80 until total mRNA was extracted with miRNeasy kit (Qiagen) according to manufacturer's protocol. RNA quality and quantity were checked using Nanodrop. RNA was conserved in RNase free water at −80° C. until analysis. RNA was converted to cDNA using the HighCapacity cDNA Reverse Transcription Kits (Applied Biosystems). Quantitative PCR was performed using TaqMan PreAmp Master Mix Kit (Applied Bioscience) and the TaqMan Gene Expression Master Mix (Applied Bioscience) following the manufacturers' protocols. Gene expression was normalized to the house-keeping gene Glyceraldehyde 3-phosphate dehydrogenase (GADPH) and normalized for each condition as 1,8e (Ct GADPH-Ct target gene)×10000.

Table 9(A-B) and 10(A-B) show representative results of the activity of ABA ex vivo on some lesional transcript of relevance for psoriasis and atopic dermatitis, respectively. In table 9 ABA decrease DEF-4 expression, a gene whose expression is increased lesional psoriatic skin, that depends on the IL-17 pathway, and that its decrease by therapies related to clinical efficacy of potent anti-psoriatic treatments. Interestingly, ABA have also impact on Th2-dependent gene expression in atopic dermatitis lesions such as CCL13, CCL17, CCL26, and IL-13. Those selected genes are of special interest in the atopic dermatitis transcriptoma since their decrease is associated to anti-inflammatory activity of effective therapies.

TABLE 9A

| Transcript relevance in psoriasis (Percentage inhibition vs media (normalized)) | |
|---|---|
| mRNA | ABA |
| IL-8 | −71.5 |
| IL-20 | −27.8 |
| ICAM-1 | −40.6 |
| LNC2 | −45.7 |
| DEF-4 | −64.8 |
| K-16 | 24.9 |

Particular results of the patient with psoriatic plaque were:

TABLE 9B

| % of inhibition vs Media (normalized) | | |
|---|---|---|
| | ABA | dexamethasone |
| IL-23A | | |
| CXCL10 | 140.1 | 8.7 |
| IL-8 | −71.5 | −70.1 |

TABLE 9B-continued

| % of inhibition vs Media (normalized) | | |
|---|---|---|
| | ABA | dexamethasone |
| IL-20 | −27.8 | 5.5 |
| ICAM-1 | −40.6 | 17.1 |
| LNC2 | −45.7 | 96.3 |
| DEF-4 | −64.8 | −15.7 |
| K-16 | 24.9 | 27.8 |
| IFNg | −10.7 | 72.7 |
| IL-17A | 9.3 | 116.9 |

TABLE 10A

| Transcript relevance in atopic dermatitis (Percentage inhibition vs media (normalized)) | |
|---|---|
| mRNA | ABA |
| CCL13 | −59.2 |
| CCL17 | −70.1 |
| CCL18 | −72.9 |
| CCL26 | −44.2 |
| IL-13 | −79.0 |

Particular results of the patient with atopic dermatitis plaque were:

TABLE 10B

| % of inhibition vs Media (normalized) | | |
|---|---|---|
| | ABA | dexamethasone |
| CCL13 | −59.2 | 28.4 |
| CCL17 | −70.1 | −81.4 |
| CCL18 | −72.9 | −9.1 |
| CCL26 | −44.2 | −34.0 |
| LOR | −45.5 | 189.2 |
| FLG | 8.3 | 270.4 |
| K16 | −69.1 | −39.8 |
| IFNg | 9.2 | −100.0 |
| IL-13 | −79.0 | −100.0 |

It is known from literature that many of these inflammatory markers are linked with the expression of toll-like receptor (TLR). These receptors are a group of glycoproteins that function as surface transmembrane receptors involved in innate immune response. They specifically detect molecular patterns commonly present and conserved among similar groups of microorganism, the pathogen-associated molecular patterns (PAMPs). TLR are in the membranes of cells, as well as in endoplasmic reticulum and endosomes. Psoriasis, acne and atopic dermatitis are skin conditions related to the function of TLRs (see, Valins et al., "The expression of Toll-like Receptors in Dermatological Diseases and the Therapeutic effect of current and newer Toll-like Receptors modulators", Journal of Clinical Aesthetic Dermatology, 2010, vol. no. 3(9)). In acne large amounts of TLR-2 have been found expressed on perifollicular and peribulbar macrophages. The production of inflammatory cytokines IL-6, IL-8 and IL-12 is clearly dependent of the interaction of *P. acnes* and TLR2. In atopic dermatitis, the increased susceptibility to infections is explained in part due to the reduced amount of antimicrobial peptides. Defects in the TLRs have been identified in AD. In Psoriasis, *M. furfur*, which is related to the development of psoriatic scalp lesions, has been found to upregulate TLR2 mRNA expression in human keratinocytes. IL18 gene expression has been inhibited with anti-TLR2 antibodies.

An extension relation of atopic dermatitis with the microbiome is also disclosed in bibliography (see Powers et al., "Microbiome and pediatric atopic dermatitis", Journal of Dermatology 2015, vol. no. 42, pp.: 1137-1142)

Therefore, it can be said that biofilm formation in these skin disorders do provoke activation of TLR, which activation is further translated to the expression of inflammatory markers as the ones that have been studied in this example. Nonetheless, as illustrated in Example 1 for the composition comprising 30% of *Morinda citrifolia* cell lysate and $30\times10^{-4}$% of abscisic acid, TLR will be blocked at least by ABA, and so the inflammatory markers will decrease.

In all assayed skin biopsies of psoriasis and atopic dermatitis, expression of the gens LOR and FLG, from Loricrin and Filaggrin, respectively, were also analyzed. These are genes that avoid stratum corneum be degraded. Tested ABA compositions altered the level of expression of these genes in an opposed mode than dexamethasone does. Thus, its effect in stratum corneum will be more effective than those performed by dexamethasone. The stratum corneum is the outermost layer of the epidermis, consisting of dead cells (corneocytes). This layer is composed of 15-20 layers of flattened cells with no nuclei and cell organelles. Their cytoplasm shows filamentous keratin. These corneocytes are embedded in a lipid matrix composed of ceramides, cholesterol, and fatty acids.

This effect of protection of stratum corneum is not observed in prior art compositions usually used in psoriasis and/or atopic dermatitis treatment, by which stratum corneum is degraded.

This assay with full-thickness lesioned skin biopsies from untreated atopic dermatitis and psoriasis patients was repeated with a *Curcuma longa* cell culture lysate comprising ABA ($30\times10^{-4}$%).

This cell culture lysate was a callus cell lysate and it was used at a final concentration of 20 μg/ml of media (KBM medium supplemented with $Ca_2Cl$ as in the assay with ABA alone). As positive or comparative control, dexamethasone (1 μM in the culture) was used.

The *Curcuma longa* cell culture lysate is obtainable by a) cultivating plant cells of *Curcuma longa* in a Murashige & Skoog (MS) medium supplemented with the plant hormones auxins and plant cytokines, and maintaining the culture by sub-culturing from each 14 to 21 days, in particular with an inoculum of ¼ of the growing medium; b) adding one volume of culture of step a), previously grown during a period from 14 to 21 days, to three volumes of a culture medium again Murashige & Skoog (MS) medium supplemented with the plant hormones auxins and plant cytokines and methyl jasmonate (500 μM in cell culture), and maintaining the culture from 10 to 18 days; and c) lysing the plant cell culture to obtain a plant cell lysate, using a Turrax and/or Sonicator This plant cell culture lysate of *Curcuma longa* comprises polyphenols, phytosterols and diarylheptanoics (curcuminoids). The amounts of polyphenols, and of diarylheptanoics (curcuminoids) can be determined in the cell culture lysates using any colorimetric method. Phytosterols using thin layer chromatography (TLC).

Patients from which biopsies were obtained included 5 psoriatic cases and 3 atopic dermatitis cases.

In psoriatic plaques, the *C. longa* callus lysate showed gene modulation activity for DEF-4 (about 60% of reduction of this marker was observed in two patients), K-16 (expression reduced over 60% in two patients) and CXCL10 (In three patients a diminution about 70-100 regarding the medium (negative control) was observed).

Particular results of one patient with psoriatic plaque were that of Table 9C:

TABLE 9C

| % of inhibition vs Media (normalized) | |
|---|---|
| | *C. longa* callus lysate with ABA |
| IL-8 | 207.4 |
| IL-20 | 49.5 |
| ICAM-1 | 61.2 |
| LNC2 | 113.7 |
| DEF-4 | −59.6 |
| K-16 | −59.2 |

In patients with atopic dermatitis, an illustrative example of the patients is depicted in table 10C below:

TABLE 10C

| Transcript relevance in atopic dermatitis (Percentage inhibition vs media (normalized)) | |
|---|---|
| mRNA | *C. longa* callus lysate with ABA |
| CCL13 | −57 |
| CCL17 | −59 |
| CCL18 | −55 |
| CCL26 | −29 |
| K-16 | −72 |
| IL-13 | −72 |

Table 9C (psoriasis) and 10C (atopic dermatitis) show that *C. longa* callus lysate decreased DEF-4 expression, a gene whose expression is increased in lesional psoriatic skin, that depends on IL-17 pathway, and that its decrease by therapies relates to clinical efficacy of potent anti-psoriatic treatments. In addition, *C. longa* callus lysate comprising ABA had also impact on Th2-dependent gene expression in atopic dermatitis lesions such as CCL13, CCL17, CCL26, and IL-13. These are genes of special interest in the atopic dermatitis transcriptome, since their decrease is associated to anti-inflammatory activity of effective therapies (Dupilumab in Dupixent® for moderate-to-severe atopic dermatitis).

In order to further characterize the properties of the *C. longa* cell lysate, additional test were performed in vitro an ex vivo.

In vitro assays with *C. longa* cell lysate:

In human monocytes line THP-1 (derived from patients with acute monocytic leukemia) inflammation was induces with IL-17 (3 ng/ml of culture) and lipopolysaccharide (LPS; 10 μg/ml) for 6 hours. After that different doses of the *C. longa* callus lysate were added (200 μg/ml, 20 μg/ml, 1 μg/ml and 0.1 μg/ml) for 24 hours. The assay was performed in 96-well plates. Tumoral necrosis factor alpha (TNF-α) and interleukine-8 (IL-8) levels were quantified by ELISA (fluorimetry, BD OpEIA, USA). One control was an assay with only the inflammatory agents at the same concentration to induce inflammation. Another control was were dexamethasone (10 μM)+Il-17/LPS.

The cell lysate comprising ABA completely restored TNF-α levels from inflamed cells. The effect was highly potent in all tested doses of the cell lysate, and of up −97%. Dexamethasone gave a value of −56% in relation to inflamed cells.

The cell lysate comprising ABA also completely restored IL-8 levels from inflamed cells. The effect was highly potent in all tested doses of the cell lysate, and of up −78%. Dexamethasone gave a value of −33% in relation to inflamed cells.

Another in vitro assay conducted with the *C. longa* callus lysate with glycerine (Turmeria Zen PRCF®) aimed to test the wound healing properties. This was performed in human dermal fibroblasts (HDF), wherein a concentration of 0.25 μg/ml of the cell lysate with ABA was able to produce a higher healed area than controls (fetal bovine serum at 10% w/w in the culture; FBS, and transforming growth factor Beta-1 at 15 ng/ml in the culture, TGF-β1) after a 2 mm wound (made by scratch) was submitted to all the tested compounds. Healing area (growth of cells) was visualized by microscope using the Image J software.

Ex vivo assays with *C. longa* cell lysate:

Human organotypic skin explant culture (hOSEC) were treated to induce stress (hydrocortisone 10 μg/ml daily) for 12 days. *C. longa* cell lysate was applied at 2%, 1% and 0.5% in the explant culture. Collagen content (measured by Collagen Dye Reagent) and Elastin content (measured using the dye label 5,10,15,20-tetraphenyl-21H,23H-porfine tetrasulfonate and Elastin precipitating Reagent) was determined. In all tested concentrations an increased elastin and collagen production was observed avoiding hydrocortisone effects.

An ex vivo wound healing assay was also carried out with punch biopsies (6 mm diameter) taken from donated skin. After an epidermis wound, re-epithelization was observed when treated with cell lysate (50 μg/ml) in a higher extent that when using epidermal growth factor (EGF) as positive control.

Example 5

Assay on Individuals with Acne. In Vivo Data

Focus on the fact that one of the causes in acne is biofilm formation and in vivo test was performed with composition comprising 30% of *Morinda citrifolia* cell lysate and $30\times10^{-4}$% of abscisic acid ((+)-(S)-cis,trans-abscisic acid), glycerine and preservatives (q.s. 100%). These actives were applied within a cream at 1.0% by weight in the cream. This assay also serves as basis of biofilm formation in biotic surfaces (skin) by microorganisms, as well as an example of the effectivity of the tested compositions that inhibiting said biofilm due to its quorum sensing inhibitor capacity.

Placebo cream: Facial cream D P7VY: water, propylene glucol, glyceryl stearate SE, caprylic/capric tryglyceride, cetearyl ethylhexylhexanoate, *Helianthus annuus* (sunflower) seed oil, tocopherol, C12-10 acid PEG-8 esther (Emulpharma® 15), decyl oleate, *Butyrospermum parkii* (shea) butter, tropolone, caprylyl glycol, 1,2-hexanediol (Symdiol® 68T), triethanolamine, carbomer (Carbopol® 934), phenoxyethanol, cetyl phosphate (Amphisol® A), fragrance/parfum, BHT.

A double blind intra-individual study vs placebo was performed in a panel of 20 volunteers (age 12-29 years, men and women with acne prone skin). The cream was applied hemi-face vs placebo. Treatment was for 30 days (with two applications per day). Sebum level production (Sebumeter SM815), pore size reduction, quantification of *P. acnes*, *S. aureus*, and *S. epidermidis*, and HD-visioface macrographies were evaluated to see the dermatological evolution of acneic lesions.

The sebum level in treated areas was about 65 μg/cm3 of skin, and it supposed a reduction of 29% in relation with the placebo. Pore size was also reduced in treated areas as well as the number of pores (−49% of pores in treated areas vs placebo). After 30 days of treatment, population of *S. aureus* was decreased at −50.65%; that of *P. acnes* had a reduction of −22.54%; and *S. epidermidis* increased 1.21%. Therefore, the tested active ingredients decreased the relative proportion of virulent bacteria (*S. aureus* and *P. acnes*) while they increased the most favorable skin microbiota in acne (*S. epidermidis*). In other words, the tested actives re-balanced the microbiota of acne prone skin, and this was done by affecting quorum sensing networks by means of abscisic acid in particular grade. The composition was able to maintain healthy skin bacterial flora, and to avoid dysbiosis causing acne.

Example 6

Preparation of *Morinda Citrifolia* and *Oleae Europaea* var. *Sylvestris* Cell Lysate Plant cell culture lysate of *Morinda citrifolia* used in the examples above was obtained by a) cultivating plant cells *Morinda citrifolia* in a Murashige & Skoog (MS) medium supplemented with the plant hormones auxins and plant cytokines, and maintaining the culture by sub-culturing from each 14 to 21 days, in particular with an inoculum of ¼ of the growing medium;

b) adding one volume of culture of step a), previously grown during a period from 14 to 21 days, to three volumes of a culture medium again Murashige & Skoog (MS) medium supplemented with the plant hormones auxins and plant cytokines and methyl jasmonate (500 μM in cell culture), and maintaining the culture from 10 to 18 days; and c) lysing the plant cell culture to obtain a plant cell lysate, using a Turrax and/or Sonicator.

This plant cell culture lysate of *Morinda citrifolia* comprises polyphenols, anthraquinones, terpenoids, flavonoids and phytosterols. The amounts of polyphenols, terpenoids and flavonoids can be determined in the cell culture lysates using any colorimetric method. Anthraquinones by HPLC, and phytosterols using thin layer chromatography (TLC).

This lysate of a plant cell culture of *Olea europaea* comprises polyphenols that can be determined by means of any colorimetric method.

All these cell culture lysates can then be submitted to lyophilization or spray drying in order to evaporate water (mainly) and for preserving the lysate. Alternatively, the cell culture lysate can be kept under controlled temperature in liquid suspension and if needed appropriate conservatives are added.

Example 7

Combination of ABA and Methyl Jasmonate

Inventors also tested the effect of methyl jasmonate in *P. acnes, S. aureus, M. furfur* and *P. aeruginosa*. It was determined that methyl jasmonate had a high bacteriostatic/fungistatic effect on *P. aeruginosa*, when used in a percentage by weight in the culture media from 15% to 30% w/w. A bactericide effect was detected at 60% w/w.

So that, combinations of either 30 μg/ml or 60 μg/ml of ABA ((+)-(S)-cis,trans-abscisic acid) with a percentage by weight of either 15% or 30% of methyl jasmonate are useful to avoid biofilm formation in a wide microbial spectra.

Example 8

Bacteriostatic or Fungistatic Effect of ABA and Plant Cell Culture Lysates of Several Plants Following the same scheme and procedure as in Examples 1-3 above, ABA 8((+)-(S)-cis,trans-abscisic acid)) and combinations of ABA with cell culture lysates or methyl jasmonate were tested on several microorganisms forming biofilms. As before, underlined concentrations are the considered bacteriostatic or fungistatic amounts and that they avoid biofilm formation.

Next Table 11 shows tested compounds and combinations:

TABLE 11

| Product | Concentrations | | | | | | |
|---|---|---|---|---|---|---|---|
| ABA | 60 μg/ml | 50 μg/ml | 40 μg/ml | 30 μg/ml | | | |
| *Morinda citrifolia* cell lysate + ABA (30 μg/ml) | 30% | 25% | 20% | 15% | 10% | 5% | |
| Methyl jasmonate + ABA | 60 μg/ml + 45 μg/ml | 35 μg/ml + 45 μg/ml | 15 μg/ml + 45 μg/ml | 60 μg/ml + 30 μg/ml | 35 μg/ml + 30 μg/ml | 15 μg/ml + 30 μg/ml | 35 μg/ml + 60 μg/ml | 15 μg/ml + 60 μg/ml |

% by weight of cell lysates and μg/ml are defined in relation to total weight or volume of the culture media in which the assay was performed.

On the hand, the plant cell culture lysate of *Olea europaea* was obtained, similarly, by:

a) cultivating plant cells *Olea europaea* in Rugini Olive Medium medium comprising plant (auxins and plant cytokines), and maintaining the culture by sub-culturing from each 14 to 21 days, in particular with an inoculum of ¼ of the growing medium;

b) adding one volume of culture of step a), previously grown during a period from 14 to 21 days, to two volumes of a culture medium again Rugini Olive Medium medium comprising the plant hormones and methyl jasmonate, and maintaining the culture from 10 to 18 days; and c) lysing the plant cell culture to obtain a plant cell lysate with a Turrax and/or Sonicator.

Assays were performed with the following microorganisms:

| Microorganism | Type Culture Collection |
|---|---|
| MRSA | DSM 11729 (commercially available) |
| *Streptococcus pyogenes* | DSM 11728 (commercially available) |
| *Candida albicans* | DSM 3454 (commercially available) |

-continued

| Microorganism | Type Culture Collection |
|---|---|
| *Corynebacterium striatum* | DSM 20668 (commercially available) |
| *Staphylococcus aureus* | CECT239 (commercially available) |
| *Streptococcus mutans* | DSM 20523 (commercially available) |

-continued

| Microorganism | Type Culture Collection |
|---|---|
| *Epidermophytum floccosum* | DSM 10709 (commercially available) |

Biofilm generation conditions and medium for the growth of the bacteria were those recommended by the supplier of each microorganism.

Results are depicted in table 12.1-12.7 below:

TABLE 12.1

| MRSA DSM11729 | | | | | | | | | | | | |
|---|---|---|---|---|---|---|---|---|---|---|---|---|
| | | | Concentration of tested *Morinda citrifolia* cell lysate (% by weight in the culture) + ABA (μg/ml) | | Concentration of tested methyl jasmonate (μg/ml) + ABA (μg/ml) | | | | | | | |
| | Inoc. Day MRSA | MRSA control | 30%(*) + 30 μg/ml | 25% + 30 μg/ml | (*)60 + 45 | (*)35 + 45 | 15 + 45 | (*)60 + 30 | (*)35 + 30 | 15 + 30 | (*)35 + 60 | 15 + 60 |
| CFU | 670000 | 1650000 | 165000 | 4715 × $10^2$ | 180 | 2580 | 603 × $10^3$ | 230 | 219 × 10 | 725 × $10^3$ | 371 × 10 | 8415 × $10^2$ |

(*)bactericide concentration

TABLE 12.2

| *Streptococcus pyogenes* DSM 11728 | | | | | | | | | | | | |
|---|---|---|---|---|---|---|---|---|---|---|---|---|
| | | | Concentration of tested *Morinda citrifolia* cell lysate (% by weight in the culture) + ABA (μg/ml) | | | | Concentration of tested methyl jasmonate (μg/ml) + ABA (μg/ml) | | | | |
| | Inoc. Day *S. Pyogenes* | *S. Pyogenes* control | (*)30% + 30 μg/ml | 25% + 30 μg/ml | 20% + 30 μg/ml | 15% + 30 μg/ml | (*)60 + 45 | (*)35 + 45 | (*)60 + 30 | (*)35 + 30 | (*)35 + 60 |
| CFU | 115000 | 810100 | 375 × $10^2$ | 975 × $10^2$ | 11375 × 10 | 117 × $10^3$ | 19 × $10^2$ | 1725 | 231 × 10 | 142 × $10^2$ | 196 × $10^2$ |

(*)bactericide concentration

TABLE 12.3

| *Candida albicans* DSM 3454 | | | | | | | |
|---|---|---|---|---|---|---|---|
| | | | ABA (μg/ml) | Concentration of tested methyl jasmonate (μg/ml) + ABA (μg/ml) | | | |
| | Inoc. Day *C. albic.* | *C. albic.* control | 60 | (*)60 + 45 | 35 + 45 | (*)60 + 30 | 35 + 60 |
| CFU | 264000 | 456500 | 367500 | 46700 | 289000 | 71500 | 249000 |

(*)fungicide concentration

TABLE 12.4

| *Corynebacterium striatum* DSM 20668 | | | | | | | |
|---|---|---|---|---|---|---|---|
| | | | Concentration of tested *Morinda citrifolia* cell lysate (% by weight in the culture) + ABA (μg/ml) | | | | Concentration of tested methyl jasmonate (μg/ml) + ABA (μg/ml) |
| | Inoc. Day *C. striatum* | *C striatum* control | (*)30% + 30 μg/ml | (*)25% + 30 μg/ml | (*)20% + 30 μg/ml | 15% + 30 μg/ml | 60 + 45 |
| CFU | 378000 | 6300000 | 58800 | 68500 | 109000 | 256500 | 512500 |

(*)bactericide concentration

TABLE 12.5

| Staphylococcus aureus CECT 239 | | | | | |
|---|---|---|---|---|---|
| | Inoc. Day | S. aureus | Concentration of tested methyl jasmonate (μg/ml) + ABA (μg/ml) | | |
| | S. aureus | control | 60 + 45 | 60 + 30 | 35 + 60 |
| CFU | 289000 | 1945000 | 351000 | 454500 | 296000 |

TABLE 12.6

| Streptococcus mutans DSM 20523 | | | | | | | | | |
|---|---|---|---|---|---|---|---|---|---|
| | Inoc. Day | S. mutans | ABA (μg/ml) | | Concentration of tested methyl jasmonate (μg/ml) + ABA (μg/ml) | | | | |
| | S. mutans | control | 60 | 50 | (*)60 + 45 | 35 + 45 | 15 + 45 | 35 + 60 | 15 + 60 |
| CFU | 200000 | 109000 × 10 | 268000 | 289500 | 1.2E+05 | 1.73E+05 | 1.92E+05 | 2.82E+05 | 2.99E+05 |

(*)bactericide concentration

TABLE 12.7

| Epidermophytum floccosum DSM 10709 | | | | | |
|---|---|---|---|---|---|
| | Inoc. Day E. flocc. | E. flocc. control | ABA (μg/ml) 60 | Concentration of tested *Morinda citrifolia* cell lysate (% by weight in the culture) + ABA (μg/ml) 30% + 30 μg/ml | Concentration of tested methyl jasmonate (μg/ml) + ABA (μg/ml) 35 + 60 |
| CFU | 136000 | 587500 | 287200 | 154000 | 370500 |

Conclusion: Even with other strains of microorganims, as well as with additional tested species, ABA and combinations of it with cell lysates and/or methyl jasmonate where able to maintain growth of miroorganisms under control, providing either a bacteriostatic effect or a bactericide effect.

*S. pyogenes* has been associated to psoriatic lesions. *C. albicans* is widely known as a specie for gynecological diseases (it usually colonizes the mucose membrane of vaginal tissue). *S. aureus* has been associated to atopic dermatitis. *C. striatum* is usually correlated with the unesthetical mal-odour. *S. mutans* is one of the species leading to dental decay (caries). *E. floccosum* is a filamentous fungus that causes skin and nail infections in humans, in particular mycodermatitis.

Example 9

Inhibition of Biofilm Formation on Coupons of Strains Different than that of Example 3. Synergic Effect Following procedure as disclosed in Example 3, particular compositions comprising ABA ((+)-(S)-cis,trans-abscisic acid) and cell lysate of a plant cell culture of *Morinda citrifolia* were also tested in an assay on glass coupons that also served as example of biofilm formation on abiotic surfaces. In addition, combinations of ABA and of methyl jasmonate were also tested.

Microorganisms used in this Example are the same species and strains of Example 8. Suspension of each microorganism to generate biofilm were prepared by adjusting the number of microbial cells to an average value between 1.5-5×$10^7$ cfu/ml in each specific broth medium.

Next Table 13 shows tested compounds and combinations:

TABLE 13

| Compounds | | ABA (μg/ml) | *Morinda citrifolia* cell lysate (%) + ABA (μg/ml) | Concentration of tested methyl jasmonate (μg/ml) + ABA (μg/ml) |
|---|---|---|---|---|
| Microorganisms | MRSA | | 25% + 30 μg/ml | |
| | *S. pyogenes* | | 20% + 30 μg/ml | 25 μg/ml + 60 μg/ml |
| | | | 15% + 30 μg/ml | 25 μg/ml + 45 μg/ml |
| | *C. albicans* | 60 μg/ml | | 35 μg/ml + 60 μg/ml |
| | | | | 35 μg/ml + 45 μg/ml |
| | *C. striatum* | | 15% + 30 μg/ml | 60 μg/ml + 45 μg/ml |
| | *S. mutans* | | | 35 μg/ml + 45 μg/ml |
| | *E. floccosum* | 60 μg/ml | | |

% by weight of *Morinda citrifolia* cell lysate and μg/ml are defined in relation to total weight or volume of the culture media in which the assay was performed.

Results are depicted in table 14.1-14.6 below:

TABLE 14.1

| MRSA DSM11729 on coupons | | | |
|---|---|---|---|
| | Inoc. Day MRSA | MRSA control | *Morinda citrifolia* cell lysate (%) + ABA (μg/ml) 25 + 30 |
| CFU | 600500 | 1810000 | 565000 |

Although data not shown, all tested combinations allowed growth of planktonic microorganims population in suspension. Thus, at tested concentrations, microorganism cells were viable and they were not killed.

TABLE 14.2

| *Streptococcus pyogenes* DSM 11728 on coupons | | | | | | |
|---|---|---|---|---|---|---|
| | Inoc. Day | *S pyog.* | *Morinda citrifolia* cell lysate (%) + ABA (μg/ml) | | Concentration of tested methyl jasmonate (μg/ml) + ABA (μg/ml) | |
| | *S. pyog.* | control | 20 + 30 | 15 + 30 | 25 + 60 | 25 + 45 |
| CFU | 180000 | 4700000 | 245000 | 2150000 | 1250000 | 1685000 |

Again, all tested combinations allowed growth of planktonic microorganims population in suspension.

TABLE 14.3

| *Candida albicans* DSM 3454 on coupons. | | | | | |
|---|---|---|---|---|---|
| | Inoc. Day | *C. alb.* | ABA (μg/ml) | Concentration of tested methyl jasmonate (μg/ml) + ABA (μg/ml) | |
| | *C. alb.* | control | 60 | 35 + 60 | 35 + 45 |
| CFU | 184000 | 460000 | 360000 | 200 | 200 |

As in previous assays with other microorganims, all tested combinations allowed growth of planktonic microorganims population in suspension.

TABLE 14.4

| *Corynebacterium striatum* DSM 20668 on coupons. | | | | |
|---|---|---|---|---|
| | Inoc. Day *C. str.* | *C. str* control | *Morinda citrifolia* cell lysate (%) + ABA (μg/ml) 15+30 | Concentration of tested methyl jasmonate (μg/ml) + ABA (μg/ml) 60 + 45 |
| CFU | 372500 | 5300000 | 200 | 522000 |

Planktonic growth in suspension of *Corynebacterium striatum* could be determined also with this tested assays of ABA in combination with cell lysate or with methyl jasmonate.

TABLE 14.5

| *Streptococcus mutans* DSM 20523 on coupons | | | |
|---|---|---|---|
| | Inoc. Day *S. mutans* | *S. mutans* control | Concentration of tested methyl jasmonate (μg/ml) + ABA (μg/ml) 35 + 45 |
| CFU | 108000 | 2220000 | 379000 |

Planktonic growth in suspension of *Streptococcus mutans* could be determined also with this tested assays of ABA in combination with methyl jasmonate.

TABLE 14.6

| *Epidermophytum floccosum* DSM 10709 on coupons. | | | |
|---|---|---|---|
| | Inoc. Day *E. flocc.* | *E. flocc.* control | ABA (μg/ml) 60 |
| CFU | 96667 | 374333 | 243667 |

Planktonic growth in suspension of *Epidermophytum floccosum* could be determined also with this tested assays of ABA in combination with cell lysate or with methyl jasmonate.

CITATION LIST

Nakamizo et al., "Comensal bacteria and cutaneous immunity", Semin Immunpathol-2014, DOI10.1007/500281-014-0452-6.

Wen-Ming et al, "Skin Microbiome: An Actor in the Pathogenesis of Psoriasis", Chin Med J (Engl). 2018, vol. no. 131(1), pp.: 95-98.

West et al., "Efficacy of a *Morinda citrifolia* Based Skin Care Regimen", Current Research Journal of Biological Sciences-2012, vol. no. 4(3), pp.: 310-314

Valins et al., "The expression of Toll-like Receptors in Dermatological Diseases and the Therapeutic effect of current and newer Toll-like Receptors modulators", Journal of Clinical Aesthetic Dermatology, 2010, vol. no. 3(9)

Powers et al., "Microbiome and pediatric atopic dermatitis", Journal of Dermatology 2015, vol. no. 42, pp.: 1137-1142

The invention claimed is:

1. A method for the treatment of a skin disease resulting from microbial biofilm formation and/or from dysbiosis of skin microbiota, said disease selected from the group consisting of psoriasis, atopic dermatitis, acne, seborrheic dermatitis, dandruff, folliculitis, rosacea, contact dermatitis and combinations thereof, comprising administering to a mammal in need of such treatment a pharmaceutical composition comprising:

a therapeutically effective amount of abscisic acid, a pharmaceutically acceptable salt of abscisic acid, or a pharmaceutically acceptable ester of abscisic acid; and a therapeutically effective amount of a *Morinda citrifolia* cell culture lysate;

together with pharmaceutically excipients or carriers;

wherein the abscisic acid, the pharmaceutically acceptable salt of abscisic acid, or the pharmaceutically acceptable ester of abscisic acid is in a percentage by weight from $10\times10^{-4}$% to $45\times10^{-4}$% in relation with total weight of the pharmaceutical composition; and wherein the *Morinda citrifolia* cell culture lysate is in a percentage by weight from 2% to 30% in relation with total weight of the pharmaceutical composition.

2. The method of claim 1, wherein the microbial biofilm is formed by a microorganism selected from the group consisting of *Propionibacterium acnes, Staphylococcus aureus, Pseudomonas aeruginosa, Malassezia furfur, Streptococcus pyogenes, E. coli, Candida albicans, Corynebacterium, Epidermophytum floccosum, Streptococcus mutans, Firmicutes, proteobacteria* and combinations thereof.

3. The method of claim 1, wherein the disease is psoriasis.

4. The method of claim 1, wherein the disease is atopic dermatitis.

5. The method of claim 1, wherein the disease is acne.

6. The method of claim 2, wherein the disease is psoriasis.

7. The method of claim 2, wherein the disease is atopic dermatitis.

8. The method of claim 2, wherein the disease is acne.

9. The method of claim 1, wherein the microbial biofilm is formed by *Staphylococcus aureus* and wherein the abscisic acid, the pharmaceutically acceptable salt of abscisic acid, or the pharmaceutically acceptable ester of abscisic acid is in a percentage by weight from 15x10-4% to 45x10-4% in relation with total weight of the pharmaceutical composition and wherein the *Morinda citrifolia* cell culture lysate is in a percentage by weight from 5% to 30% in relation with total weight of the pharmaceutical composition.

10. The method of claim 1, wherein the microbial biofilm is formed by *Propionibacterium acnes* and wherein the abscisic acid, the pharmaceutically acceptable salt of abscisic acid, or the pharmaceutically acceptable ester of abscisic acid is in a percentage by weight of 15x10-4% in relation with total weight of the pharmaceutical composition and wherein the *Morinda citrifolia* cell culture lysate is in a percentage by weight of 10% in relation with total weight of the pharmaceutical composition.

11. The method of claim 1, wherein the microbial biofilm is formed by *Staphylococcus aureus* and wherein the abscisic acid, the pharmaceutically acceptable salt of abscisic acid, or the pharmaceutically acceptable ester of abscisic acid is in a percentage by weight from 15x10-4% to 30x10-4% in relation with total weight of the pharmaceutical composition and wherein the *Morinda citrifolia* cell culture lysate is in a percentage by weight from 5% to 10% in relation with total weight of the pharmaceutical composition.

12. The method of claim 1, wherein the microbial biofilm is formed by *Propionibacterium acnes* and wherein the abscisic acid, the pharmaceutically acceptable salt of abscisic acid, or the pharmaceutically acceptable ester of abscisic acid is in a percentage by weight from 15x10-4% in relation with total weight of the pharmaceutical composition and wherein the *Morinda citrifolia* cell culture lysate is in a percentage by weight from 5 to 10% in relation with total weight of the pharmaceutical composition.

* * * * *